United States Patent [19]

Otvos

[11] Patent Number: 5,343,389
[45] Date of Patent: Aug. 30, 1994

[54] METHOD AND APPARATUS FOR MEASURING CLASSES AND SUBCLASSES OF LIPOPROTEINS

[75] Inventor: James D. Otvos, Apex, N.C.

[73] Assignee: North Carolina State University, Raleigh, N.C.

[21] Appl. No.: 79,223

[22] Filed: Jun. 17, 1993

Related U.S. Application Data

[63] Continuation of Ser. No. 738,052, Jul. 30, 1991, abandoned.

[51] Int. Cl.[5] ............................................. G06F 15/42
[52] U.S. Cl. ................................ 364/413.09; 436/173
[58] Field of Search ............... 364/413.07, 413.08, 364/413.09; 422/681, 87; 128/653.2; 435/111; 324/307–309; 436/63, 169, 173; 204/60 H, 180 R, 129 R

[56] References Cited

U.S. PATENT DOCUMENTS

| | | |
|---|---|---|
| 3,950,135 | 4/1976 | Whitesides et al. . |
| 4,224,031 | 9/1980 | Mee et al. . |
| 4,720,788 | 1/1988 | Golias . |
| 4,728,889 | 3/1988 | Gadian et al. . |
| 4,852,025 | 7/1989 | Herpichböhm . |
| 4,933,844 | 6/1990 | Otvos .............................. 364/413.08 |

OTHER PUBLICATIONS

T. Musliner and R. Krauss, *Clinical Chemistry* 34, B78–B83 (1988).

*Primary Examiner*—Gail O. Hayes
*Attorney, Agent, or Firm*—Bell, Seltzer, Park & Gibson

[57] ABSTRACT

A method and apparatus for analyzing blood plasma or serum to determine the concentrations of its lipoprotein constituents includes obtaining the NMR chemical shift spectrum of a sample, Stored reference NMR spectra of the constituent subclasses of major lipoprotein classes are added together to form a lineshape that best fits the measured blood plasma NMR spectrum, and from this, the concentration of each lipoprotein constituent in the blood plasma or serum is determined.

14 Claims, 13 Drawing Sheets

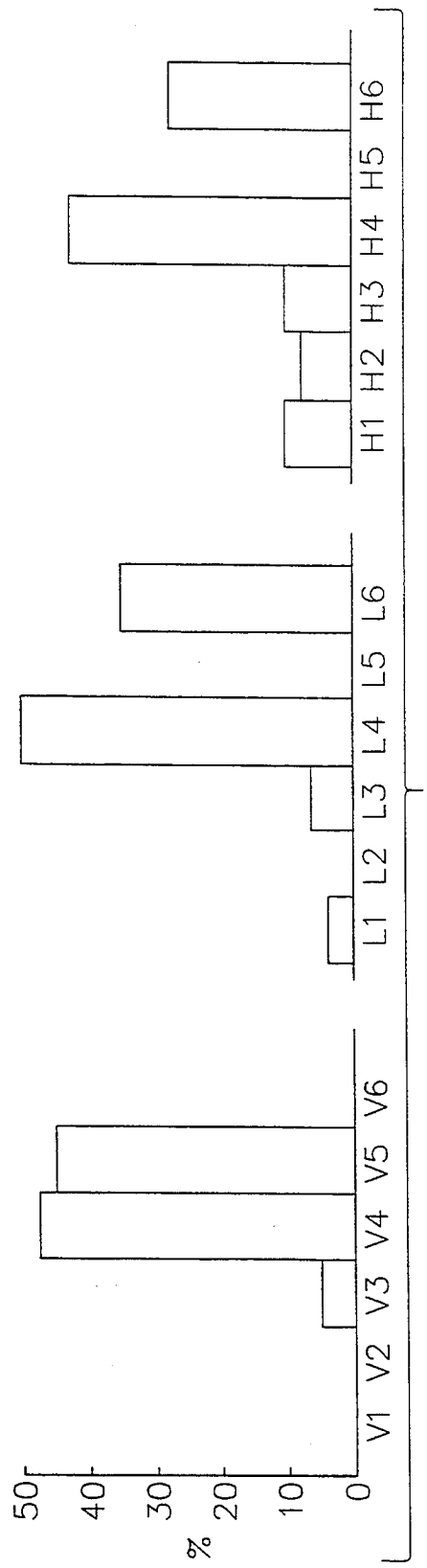
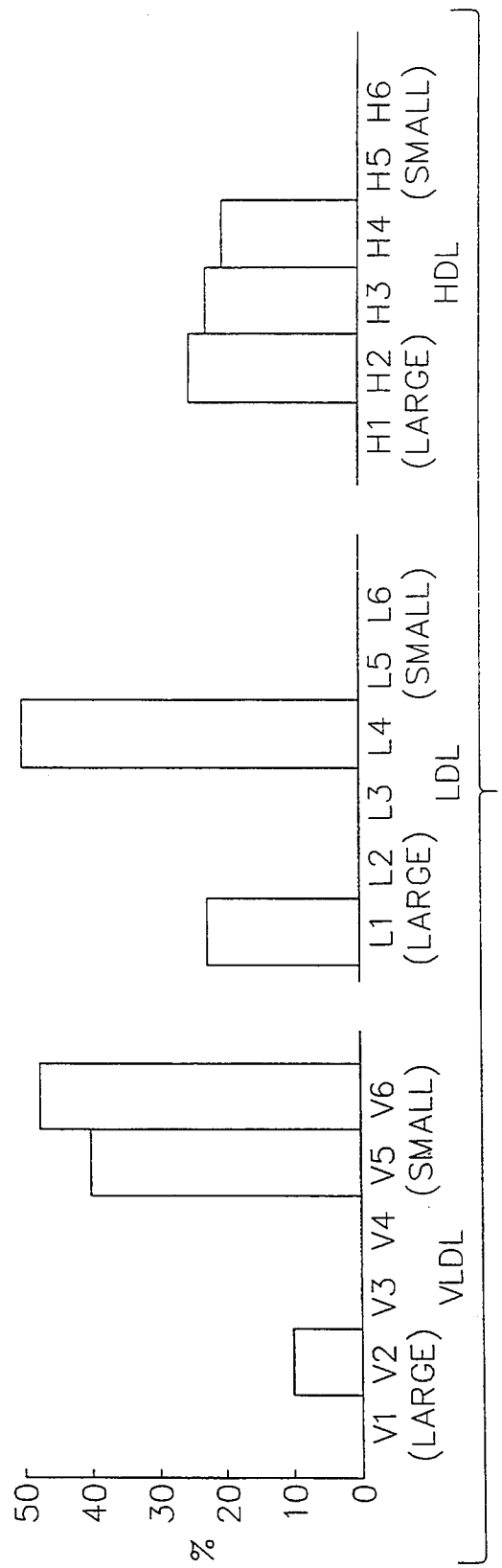
FIG. 5A.
FIG. 5B.

METHOD AND APPARATUS FOR MEASURING CLASSES AND SUBCLASSES OF LIPOPROTEINS

This invention was made with Government support under Grant No. HL43230 awarded by the National Institutes of Health. The Government has certain rights in the invention.

This is a continuation of co-pending application(s) Ser. No. 07/738,052 filed on Jul. 30, 1991, now abandoned.

FIELD OF THE INVENTION

The invention relates to the measurement of lipoprotein levels in blood plasma or blood serum and, more particularly, the levels of low-density lipoproteins (LDL), high-density lipoproteins (HDL), very low-density lipoproteins(VLDL) and subclasses thereof. These lipoproteins account for the vast majority of the cholesterol found in blood.

BACKGROUND OF THE INVENTION

The importance of accurately measuring cholesterol levels in blood is well known. The federal government, in combination with more than twenty health organizations, has launched an aggressive campaign, through the National Cholesterol Education Program, to convince physicians and the general population of the dangers of high cholesterol levels in the blood. All persons are urged to have their cholesterol levels checked, and specific treatments are recommended based on the precise measured cholesterol level. In addition, treatments are not based solely on the total cholesterol level, but instead, on the level of LDL cholesterol. LDL cholesterol appears to be the major cause of clogged arteries, whereas HDL cholesterol aids in removing cholesterol deposits. A separate, and more expensive test is required to determine the level of LDL cholesterol and it is usually not conducted unless the measured total cholesterol level is at the borderline or high risk levels.

The most common methods for measuring cholesterol levels are notoriously inaccurate and the standard practice is to repeat the measurement a number of times when high levels are detected on the first measurement. Inaccuracies of 5% or more have been found in nearly half of the measurements made by testing laboratories and 15% of the measurements were inaccurate by an amount greater than 10%. These inaccuracies are inherent in the current measurement methods which require considerable handling of the blood and certain presumptions about the ratios of its constituent parts.

Direct quantization of lipoprotein cholesterol is usually achieved by enzymatic assay of the individual lipoproteins, which are separated by ultracentrifugation, electrophoresis, or selective precipitation. There is great variability among the available separation methods in terms of accuracy, convenience, and cost. Generally, the most accurate methods are those involving ultracentrifugation, but these are very time consuming and expensive and therefore not suitable for largescale population studies. The most widely used alternative is an indirect method introduced by W. T. Friedewald, R. I. Levy, and D. S. Fredrickson, Estimation of the Concentration of Low-Density Lipoprotein Cholesterol in Plasma, Without Use of the Preparative Ultracentrifuge, *Clin. Chem.* 18, 499–502 (1972). In this procedure, plasma triglyceride (TG) and total cholesterol (TC) are measured by enzymatic assay. To a separate aliquot of plasma is added one of several reagents which selectively precipitates VLDL and LDL. After removing the precipitate by centrifugation, the supernatant is assayed for cholesterol to provide a measure of HDL cholesterol (HDL-C). An estimate of VLDL cholesterol (VLDL-C) is then made by dividing the plasma triglyceride level by five. The LDL cholesterol (LDL-C) concentration is then calculated by difference: $LDL-C = TC - (HDL-C + VLDL-C)$. Although this method is relatively rapid and inexpensive, there are several steps where experimental error can be introduced, particularly in the precipitation step. In addition, the accuracy of the analysis depends on the assumption that VLDL-C can be reliably estimated as one fifth the concentration of plasma triglyceride.

When fasting samples are used, this is generally true, but other formulas have also been suggested to give more accurate values as described by D. M. DeLong, E. R. DeLong, P. D. Wood, K. Lippel, and B. M. Rifkind, A Comparison of Methods for the Estimation of Plasma Low- and Very Low-Density Lipoprotein Cholesterol, *J. Am. Med. Assoc.* 256, 2372–2377 (1986).

It has also been shown that the major lipoprotein constituents could be further subdivided into subclasses based on further refinement of particle densities. Krauss et al, *J. Lipid Research* 23, 97–104 (1982), Atger et al., *Clinical Chemistry* 37, 1149–1152 (1991). The distribution of these subclasses within a major lipoprotein group may in itself provide further insight into risk analysis of CHD. Stossel et al, *JAMA* 260, 1917–1921 (1988). However, previous methods of determining the distribution profile of subclasses have been time consuming and unable to determine a number of subclass concentrations simultaneously.

SUMMARY OF THE INVENTION

The present invention relates to a method and apparatus for measuring the lipoprotein constituents of blood using a nuclear magnetic resonance (NMR) technique. More specifically, the method and apparatus includes acquiring proton NMR data from a sample of blood plasma or serum, processing the acquired NMR data to produce a chemical shift spectrum, and deconvoluting the spectrum in terms of the spectra of subclasses of the major classes of lipoprotein, to give the concentration of each of the lipoprotein constituents and the distribution of subclasses of the constituents. It has been discovered that the spectrum is accurately represented by a linear combination of the spectra of plasma constituents into which the blood can be fractionated. The major constituents are commonly classed according to density as VLDL, LDL, HDL, chylomicrons and protein. The NMR spectral properties of the subclasses of these classes have been found to be virtually invariant from person to person. Thus, any differences in the NMR spectra are due entirely to differences in the amplitudes of the subclass spectra, which, in turn, is due to the concentrations of the subclasses and therefore the constituents in the blood.

A general object of the invention is to provide an accurate and reliable measurement of the lipoprotein constituents of blood. Since the observed spectrum of a whole plasma sample can be closely simulated by appropriately weighted sums of the NMR spectra of the subclasses of its constituent classes, it is possible to extract the concentrations of these constituents in a sample by calculating the weighting factors which give the best fit between the sample spectrum and the calculated spectrum. The handling and processing of the sample is relatively simple compared to prior methods and there is, therefore, less opportunity for error. Furthermore, by including chylomicrons as a constituent the fasting requirement of previous methods is no longer required.

Another object of the invention is to provide a method for measuring the lipoprotein constituents of blood at an economical cost and on a mass basis. The preparation of the sample is a trivial task and the actual NMR measurement is carried out automatically by an NMR spectrometer in five minutes or less. The deconvolution calculations are also carried out automatically by a computer which prints out a report that indicates the concentrations of all of the lipoprotein subclasses. The sums of the subclass concentrations falling within a particular density range give the concentration of the lipoprotein class corresponding to that density range. Furthermore, the distribution of subclasses of constituents is developed for each constituent simultaneously.

Another object of the present invention is to provide a method which is independent of environmental variables for determining the concentrations of lipoproteins in blood. By aligning the subclass reference spectra and the sample spectra to a control peak, the line shape analysis using the deconvolution process is rendered independent of environmental variables such as temperature and sample composition.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

FIG. 5 is a series of graphs of the subclass distributions of the samples used in FIGS. 2 and 3;

GENERAL DESCRIPTION OF THE INVENTION

Figure 1:
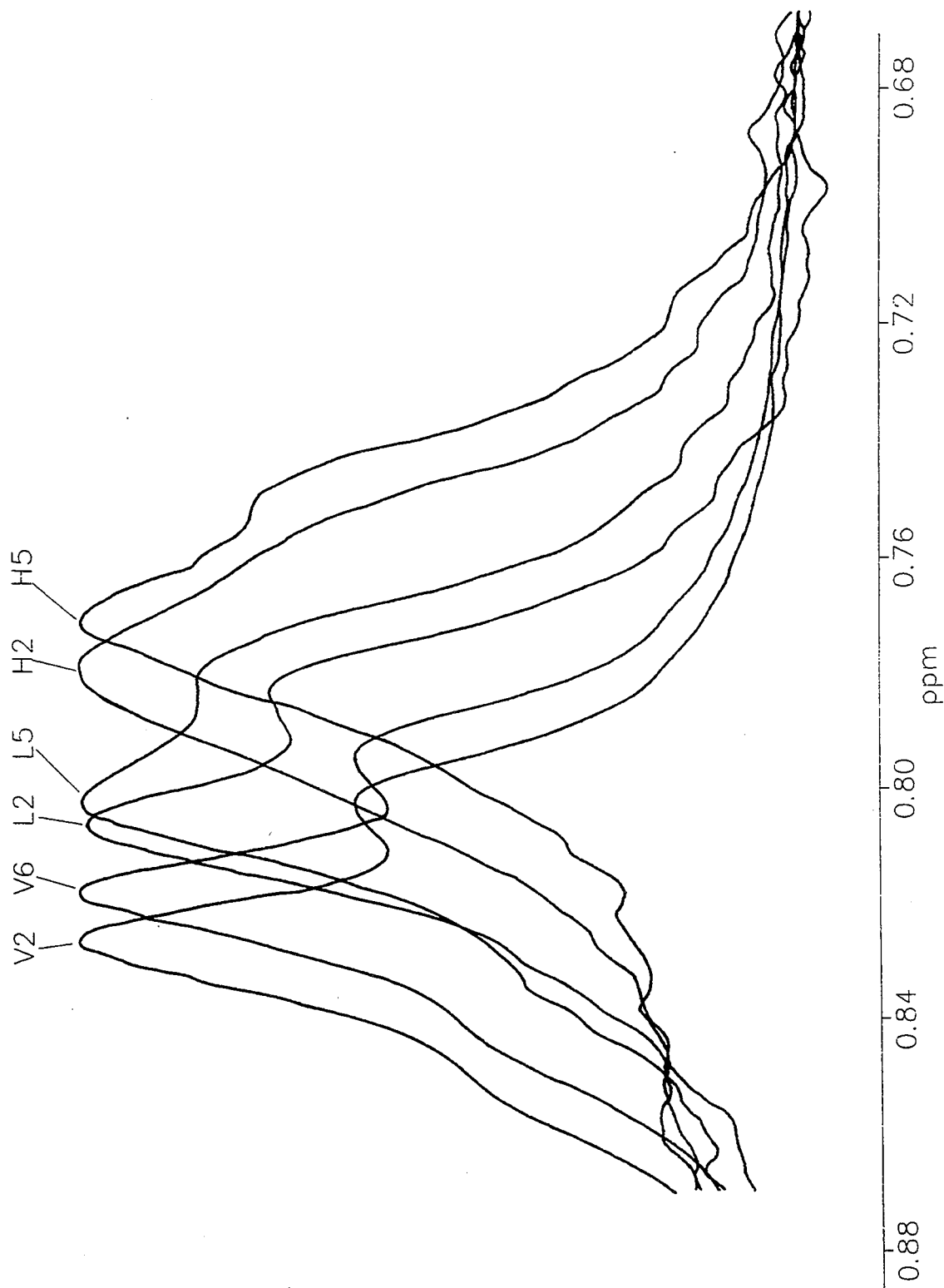
FIG. 1 is a graph showing the chemical shift spectra of a representative sample of lipoprotein constituent subclasses.

The present invention relates to the calculation of concentrations of lipoprotein constituents of blood plasma. Specifically, the present invention determines lipoprotein concentrations using the deconvolution of proton NMR spectra of plasma in much the same manner as U.S. Pat. No. 4,933,844, the specification of which is hereby incorporated herein by reference as if set out fully.

$^1$H NMR spectra of human blood plasma contain two prominent peaks centered at approximately 1.2 and 0.8 ppm (relative to the chemical shift standard, TSP). These peaks arise from methylene ($CH_2$) and methyl ($CH_3$) protons, respectively, of plasma lipids. Each of these peaks is very heterogeneous in nature, consisting of overlapping resonances from protons of the several chemically distinct classes of lipids present in plasma: triglycerides; cholesterol; cholesterol esters; and phospholipids. These lipids are packaged together into three major classes of lipoprotein particles, which differ in the proportions of lipids which they contain. These lipoprotein particles also differ in density from which their names are derived: very low density lipoprotein (VLDL), low density lipoprotein (LDL), and high density lipoprotein (HDL). These major classes of lipoprotein constituents may be further subdivided into subclasses. A subclass of lipoprotein particles comprises particles which have common physical properties, such as density, which permit a subclass to be fractionated from other subclasses and that exhibits NMR properties which are distinct from other subclasses. The NMR properties of one subclass may be distinct in a number of ways such as chemical shift or lineshape variations which make the subclass distinguishable from other subclasses. Subclasses distinguished upon density may be considered as a subclass of the class of lipoprotein which contains particles of the subclasses density.

Only that fraction of the lipids in these lipoprotein particles that are in a fluid, mobile state (as opposed to an ordered liquid-crystalline state) contribute to the plasma lipid NMR resonances. The heterogeneity of these plasma signals is reflected by their complex lineshapes, which vary from person to person owing to variations of the plasma concentrations of the different lipoprotein particles, each of which has its own characteristically different NMR spectral properties.

The method of the present invention allows the concentrations of lipoprotein particles (VLDL, LDL, HDL, and chylomicrons) of a plasma sample to be extracted from its $^1$H NMR spectrum by a computer analysis of the lineshapes of its methyl and methylene signals. Use of the methyl signal alone, however has been found to be preferable. The method exploits the finding that this region of the observed plasma spectrum is accurately represented by a simple linear combination of the spectra of subclasses of the five major lipoprotein classes into which plasma can be fractionated by differential flotation ultracentrifugation. The five classes are differentiated on the basis of their density (in kg/L) and include: VLDL (density $< 1.006$); LDL (density $= 1.006$ to $1.063$); HDL (density $= 1.063$ to $1.21$); "Protein" (density $> 1.21$) and chylomicrons (density $0.940$). The "Protein" constituent is the mostly protein-containing bottom fraction left behind after flotation of the lipoproteins. The inclusion of the chylomicron constituent eliminates the need for the blood sample to be taken from a fasting donor.

The NMR spectral properties of these classes have been found to be quite similar from person to person. This is illustrated in Table 1 which is the result of a study conducted at the University of Wisconsin-Milwaukee and the Medical College of Wisconsin.

TABLE 1

| 500 MHz NMR Parameters of the Separated Lipoprotein Constituents of Plasma | |
|---|---|
| Parameter | Mean +/− SD |
| VLDL | (n = 117) |
| $CH_2$ Chemical Shift (ppm) | 1.233 +/− 0.002 |
| $CH_3$ Chemical Shift (ppm) | 0.839 +/− 0.002 |
| $CH_2$ Linewidth (Hz) | 20.8 +/− 1.9 |
| $CH_3$ Linewidth (Hz) | 16.3 +/− 0.8 |

TABLE 1-continued

500 MHz NMR Parameters of the Separated Lipoprotein Constituents of Plasma

| Parameter | Mean +/− SD |
| --- | --- |
| CH$_2$/CH$_3$ Intensity Ratio | 3.76 +/− 0.29 |
| LDL | (n = 66) |
| CH$_2$ Chemical Shift (ppm) | 1.219 +/− 0.005 |
| CH$_3$ Chemical Shift (ppm) | 0.822 +/− 0.002 |
| CH$_2$ Linewidth (Hz) | 34.0 +/− 2.9 |
| CH$_3$ Linewidth (Hz) | 21.1 +/− 1.0 |
| CH$_2$/CH$_3$ Intensity Ratio | 1.27 +/− 0.13 |
| HDL | (n = 70) |
| CH$_2$ Chemical Shift (ppm) | 1.186 +/− 0.004 |
| CH$_3$ Chemical Shift (ppm) | 0.796 +/− 0.003 |
| CH$_2$ Linewidth (Hz) | 34.4 +/− 2.9 |
| CH$_3$ Linewidth (Hz) | 20.0 +/− 0.8 |
| CH$_2$/CH$_3$ Intensity Ratio | 1.58 +/− 0.13 |
| PROTEIN | (n = 111) |
| CH$_2$/CH$_3$ Intensity Ratio | 0.37 +/− 0.10 |

Figure 2:
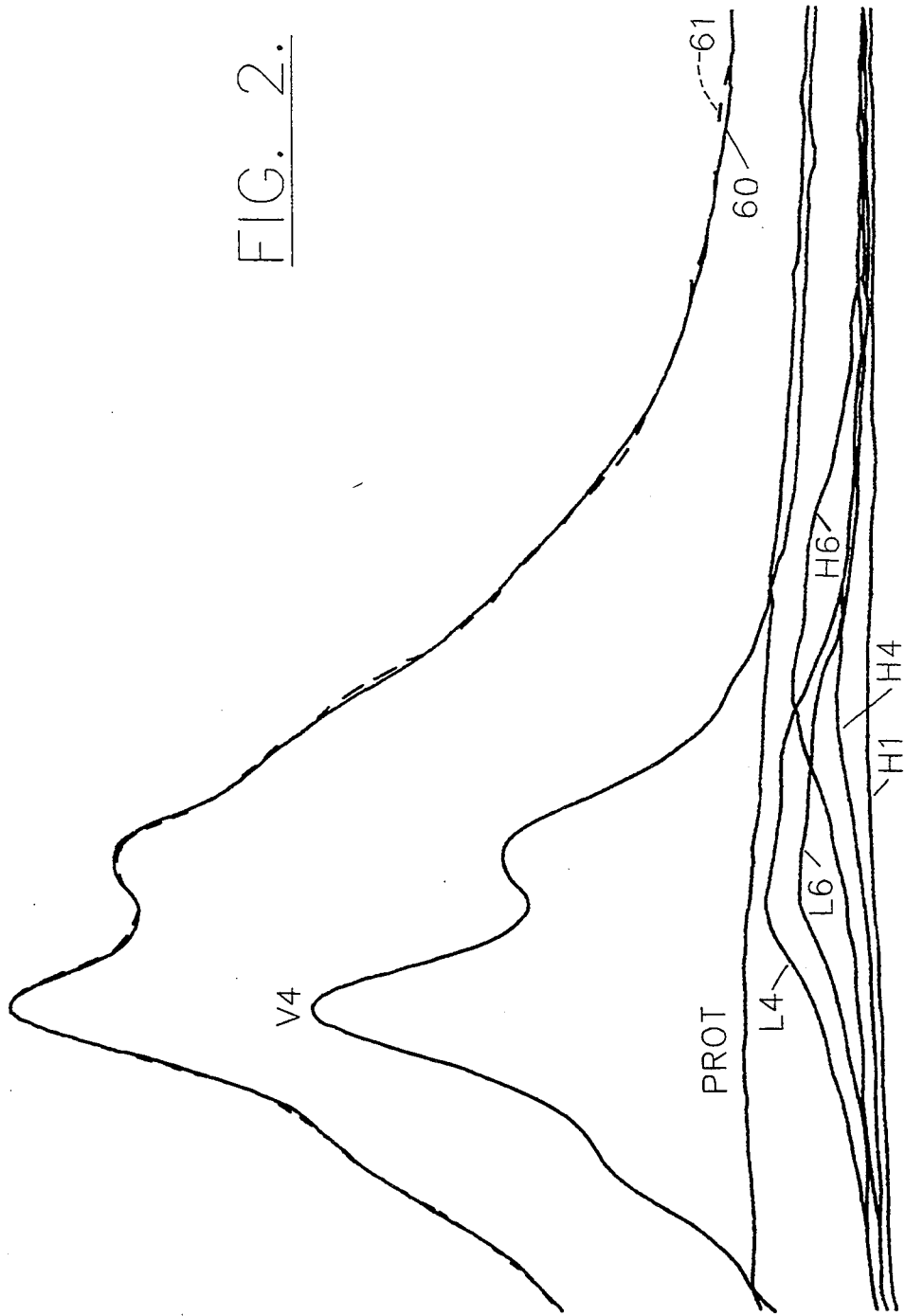
FIG. 2 is a graph showing the chemical shift spectra of a first plasma sample and its lipoprotein constituents.
Figure 3:
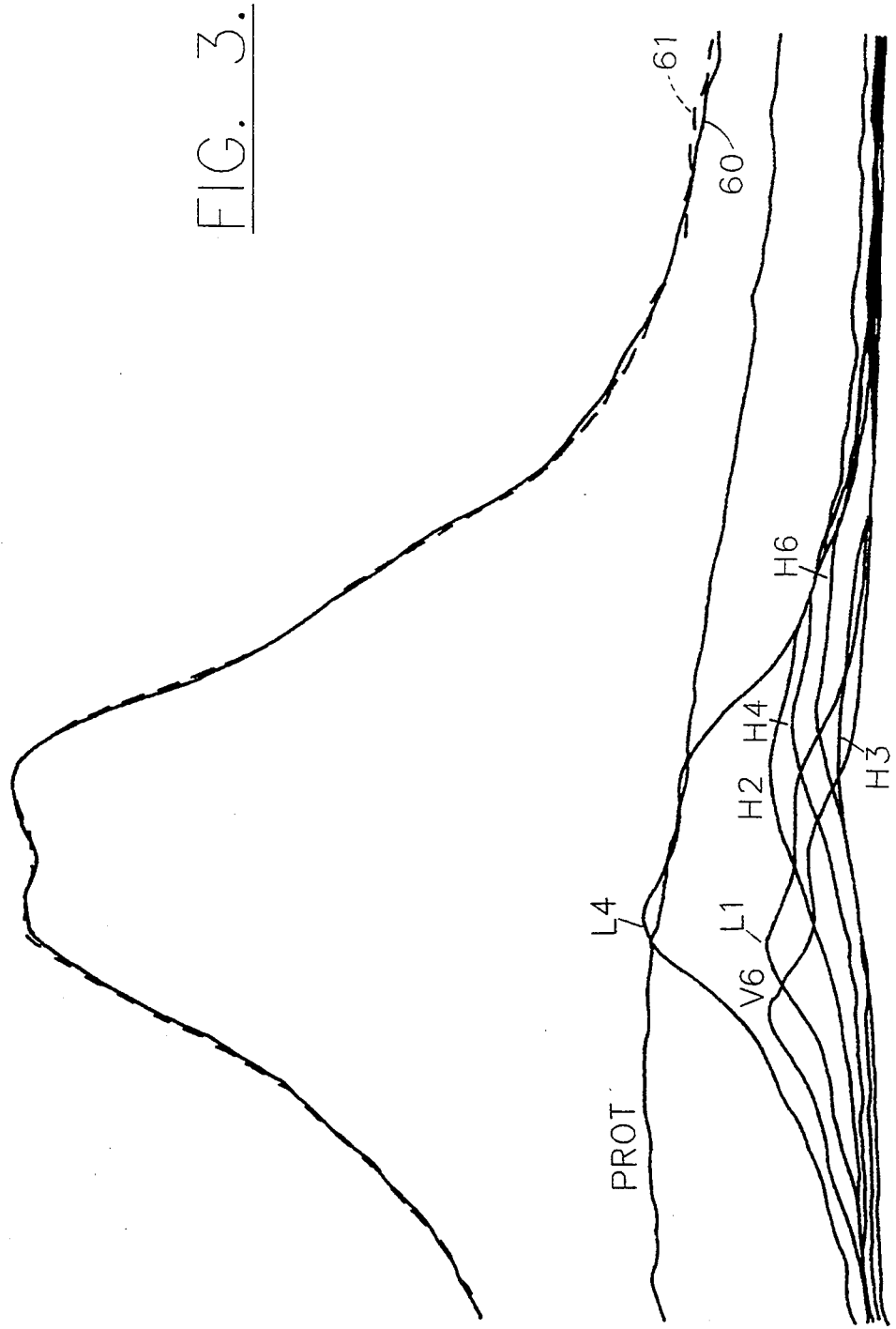
FIG. 3 is a graph showing the chemical shift spectra of a different plasma sample and its corresponding lipoprotein constituents.

The small person-to-person variations in the lineshapes of the lipoprotein classes are caused by the subclass heterogeneity known to exist within each of these lipoprotein classes. FIG. 1 shows the lineshapes and chemical shifts (positions) for a number of subclasses of lipoproteins. As shown in FIG. 1, the chemical shifts and lineshape differences between the subclasses are much smaller than those between the major lipoprotein classes, but are completely reproducible. Thus, differences among the NMR signals from the plasma of individuals are caused by differences in the amplitudes of the lipid resonances from the subclasses present in the plasma, which in turn are proportional to their concentrations in the plasma. This is illustrated in FIGS. 2 and 3 in which the NMR chemical shift spectra of two substantially different blood plasma samples are shown. The spectral peak produced by methyl (CH$_3$) protons 60 (shown as a solid line) is shown for the blood samples in FIGS. 2 and 3. The spectral peak 61 (shown as a dotted line) in FIGS. 2 and 3 is produced by the arithmetic sum of the NMR signals produced by the lipoprotein subclasses of the major classes VLDL, LDL, HDL, proteins and chylomicrons, as illustratively shown in FIG. 1. It can be seen that the lineshape of the whole plasma spectrum is dependent on the relative amounts of the lipoprotein subclasses whose amplitudes change dramatically with their relative concentrations in the plasma sample. It is the invariant lineshape of the NMR spectra of the subclasses of plasma lipoprotein constituents across the entire population and the fact that these lineshapes may be arithmetically added to produce the lineshape of the blood plasma sample, which is the basis for the present invention.

Since the observed CH$_3$ lineshapes of whole plasma samples are closely simulated by the appropriately weighted sum of lipid signals of its constituent subclasses of lipoprotein classes, it is possible to extract the concentrations of these constituents present in any sample. This is accomplished by calculating the weighting factors which give the best fit between observed blood plasma NMR spectra and the calculated blood plasma spectra. The process of NMR lipoprotein analysis is thus comprised of the following steps: (1) acquisition of an NMR "reference" spectrum for each of the pure constituent lipoprotein subclasses of plasma, (2) acquisition of whole plasma NMR spectra using measurement conditions identical to those used to obtain the reference spectra, and (3) computer deconvolution of the plasma NMR spectra in terms of the constituent subclasses to give the concentration of each lipoprotein constituent expressed as a multiple of the concentration of the corresponding lipoprotein reference. The plasma lineshape analysis is accomplished by calculating weighting coefficients for each of the reference NMR spectra which minimize the sum of squared deviations between the observed plasma NMR spectrum and that which is calculated by summing the weighted reference spectra.

The inclusion of the subclasses of the major lipoprotein classes decreases the error between the calculated lineshape and the NMR lineshape, thus increasing the accuracy of the measurement while allowing for simultaneous determination of the subclass profile of each class. Because the differences in subclass lineshapes and chemical shifts are small it is important to correctly align the reference spectrum of each subclass with the plasma spectrum. The alignment of these spectra is accomplished by the alignment of control peaks in the spectra which are known to respond in the same manner to environmental variables, such as temperature and sample composition, as do the lipoprotein spectra. One such suitable alignment peak is the peak produced by CaEDTA, although other EDTA peaks may be utilized. By alignment of the spectra, the small variations in the subclasses lineshapes and chemical shifts may be exploited to produce higher accuracy and subclass profiles.

DETAILED DESCRIPTION OF THE DRAWINGS

FIG. 1 is a graph of the chemical shift spectra of representative subclasses of plasma that serve as reference spectra in the plasma lineshape analysis. As shown in FIG. 1, the spectra labeled V2 and V6 are of chylomicrons and VLDL respectively; the spectra labeled L2 (1.006 density<1.035) and L5 (1.035<density<1.063) are of constituent subclasses of the LDL major class of plasma; and the spectra labeled H2 (1.063<density<1.125) and H5 (1.125<density<1.210) are constituent subclasses of the HDL major class of plasma. The subclasses shown in FIG. 1 are representative and further refinement of densities or sizes within a constituent lipoprotein class results in additional subclasses which may be incorporated as reference spectra. As shown in FIG. 1, the reference spectra of subclasses within a lipoprotein class exhibit substantial similarity to other reference spectra within that lipoprotein class. Furthermore, the spacing between spectra within a class is closer than between spectra of a different class. Because of the very close proximity between reference spectra for subclasses within a lipoprotein class, proper alignment of the reference spectra to the sample spectrum is essential to prevent misregistration of subclass spectra.

FIGS. 2 and 3 are graphs of the chemical shift spectra of two different blood samples and the corresponding subclass constituents obtained using the present invention. The lineshapes shown in FIGS. 2 and 3 are for the methyl peak of plasma. As shown in FIGS. 2 and 3, the calculated lineshape 61 (dashed line) of the methyl peak and the experimental lineshape 60 (solid line) closely correspond to one another. The subclasses utilized to form the calculated lineshape are also shown in FIGS. 2 and 3. The protein component of the lineshapes is also shown in FIGS. 2 and 3. FIGS. 2 and 3 illustrate the variation between individuals of the distribution of constituent subclasses within a major lipoprotein class. For example, in FIG. 3, the reference spectra for the subclasses L1, V6, H2 and H3 were utilized in calculating the lineshape whereas in FIG. 2 none of these subclasses were required. Another example is the large V4 component present in FIG. 2 which is not present in FIG. 3.

Figure 4:
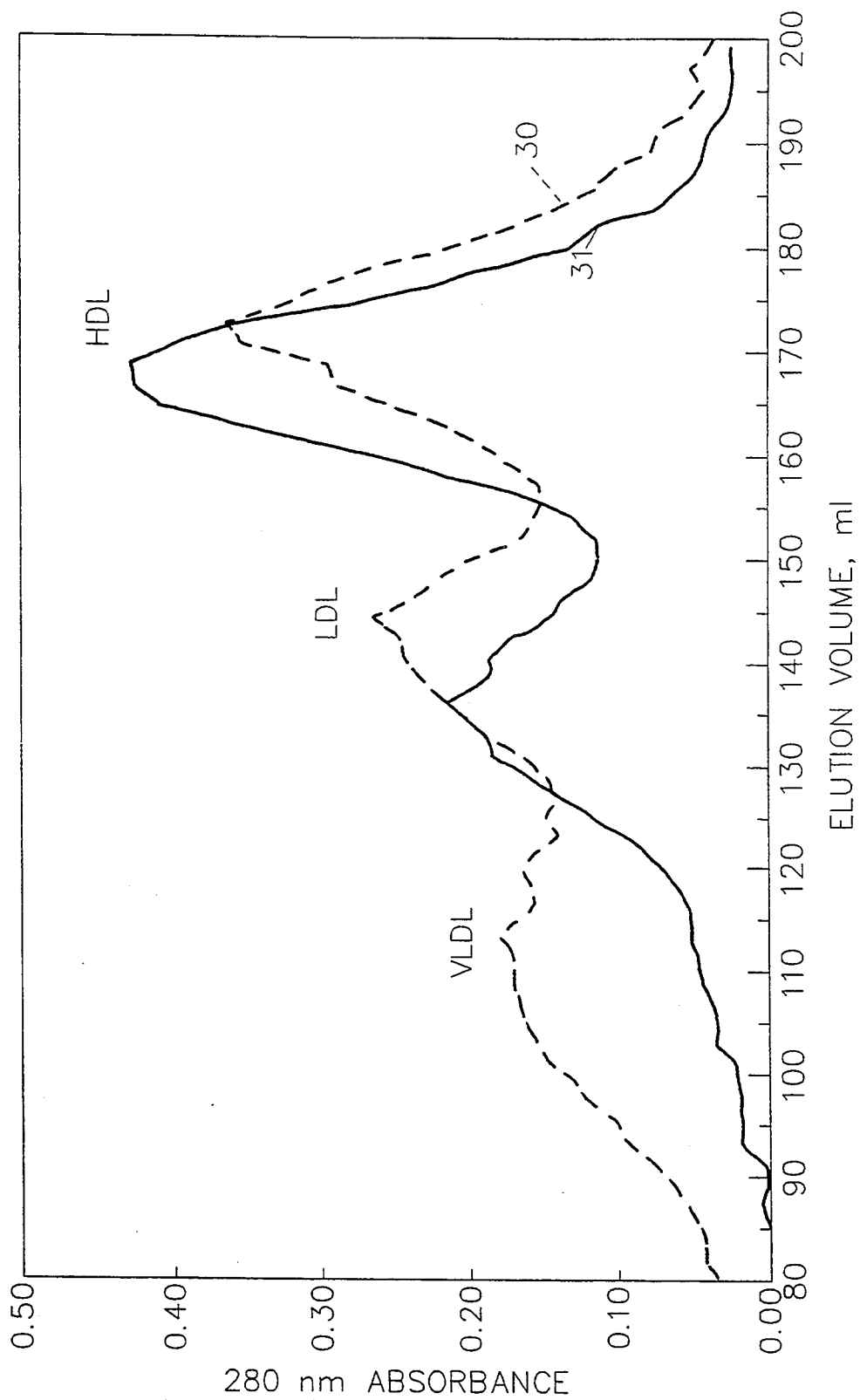
FIG. 4 is a graph showing the Agarose Gel Filtration Profile of the samples used in FIGS. 2 and 3.
Figure 6A:
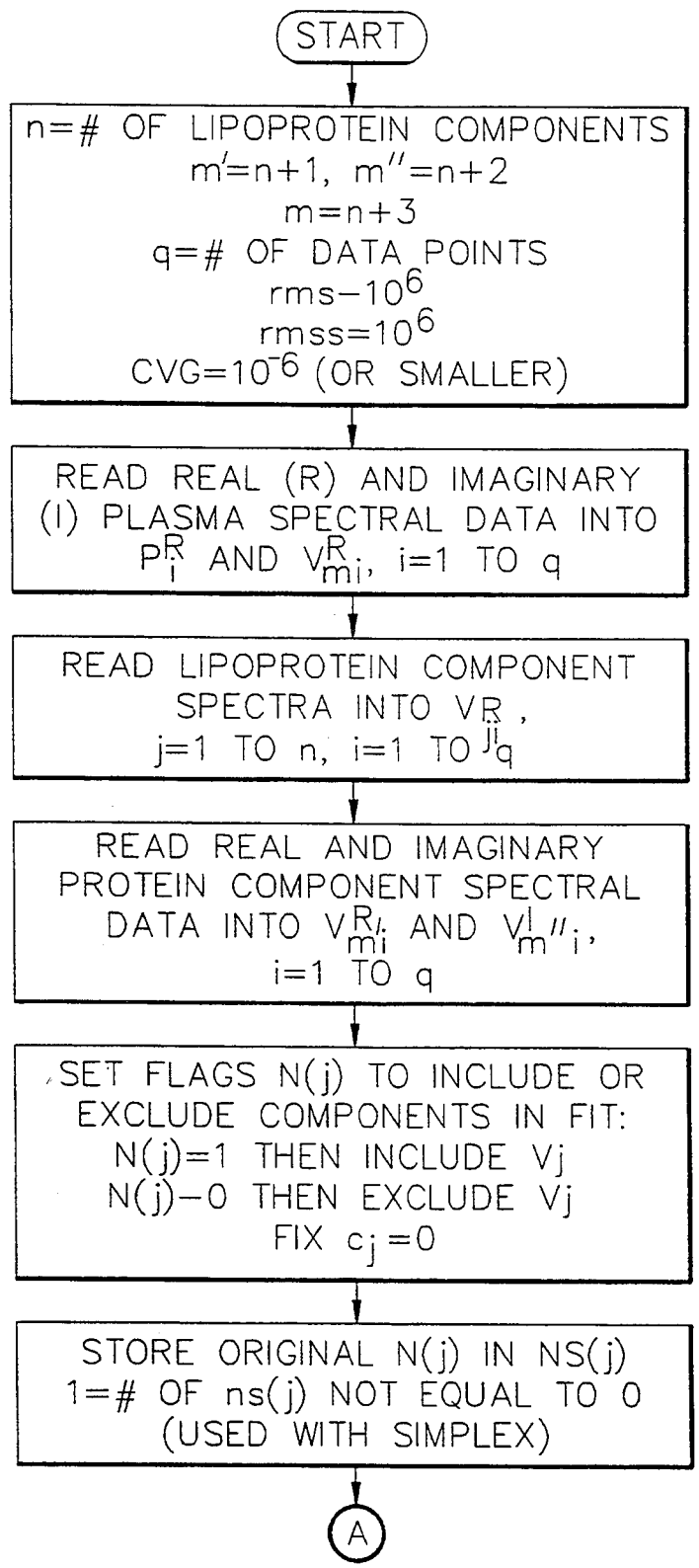
FIG. 6A–6G are a flow chart of the program for performing the method of the present invention.
Figure 6B:
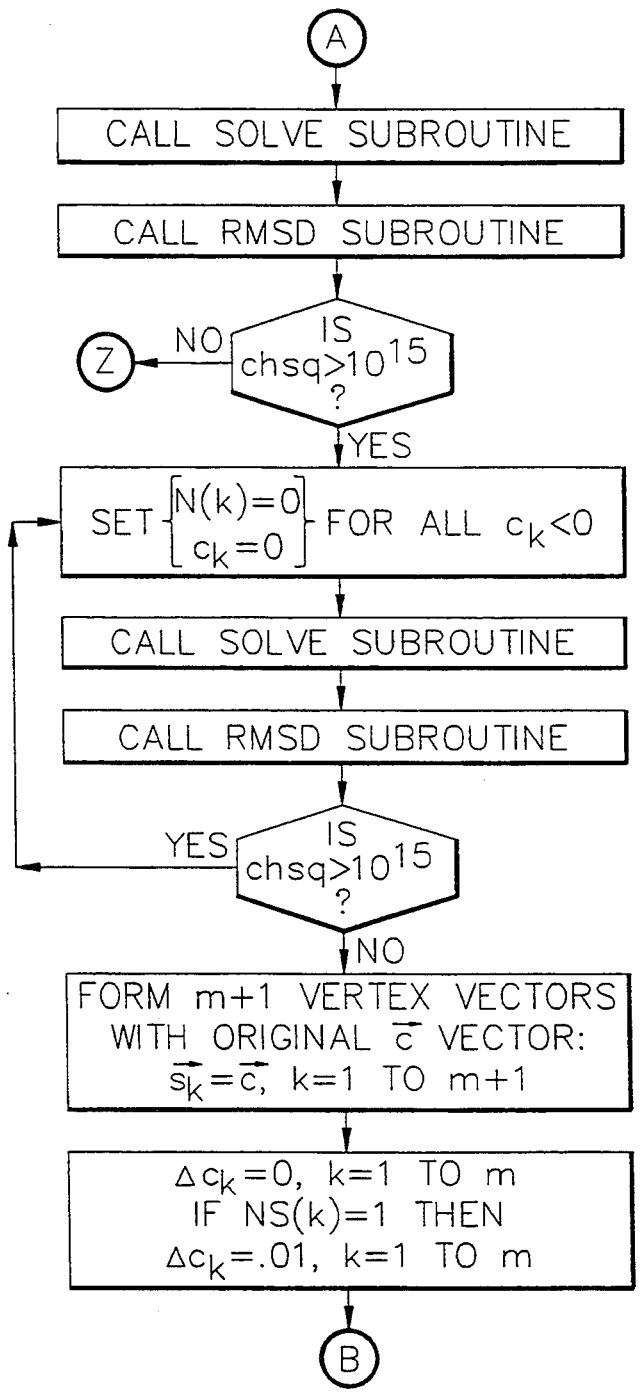
Figure 6C:
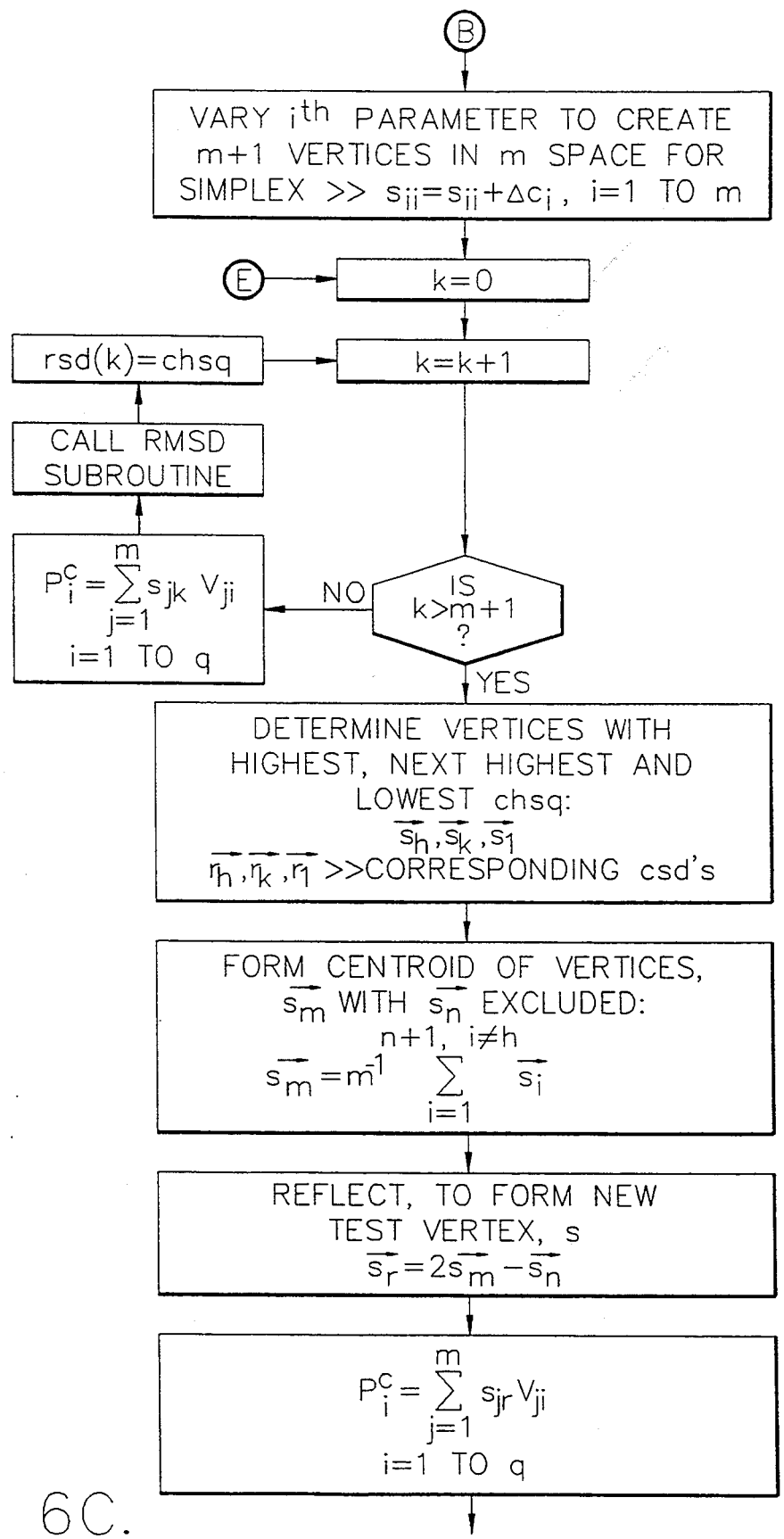
Figure 6D:
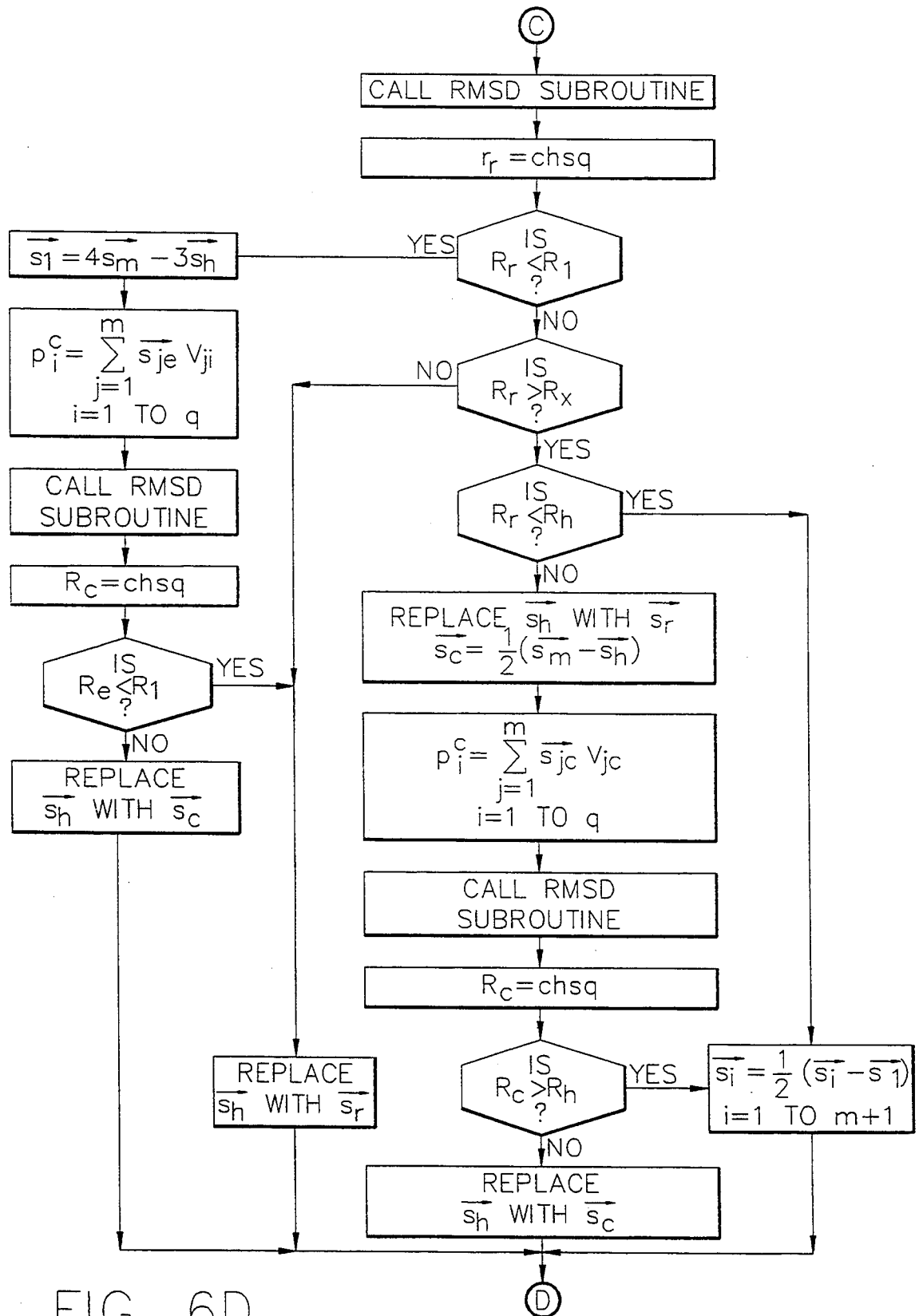
Figure 6E:
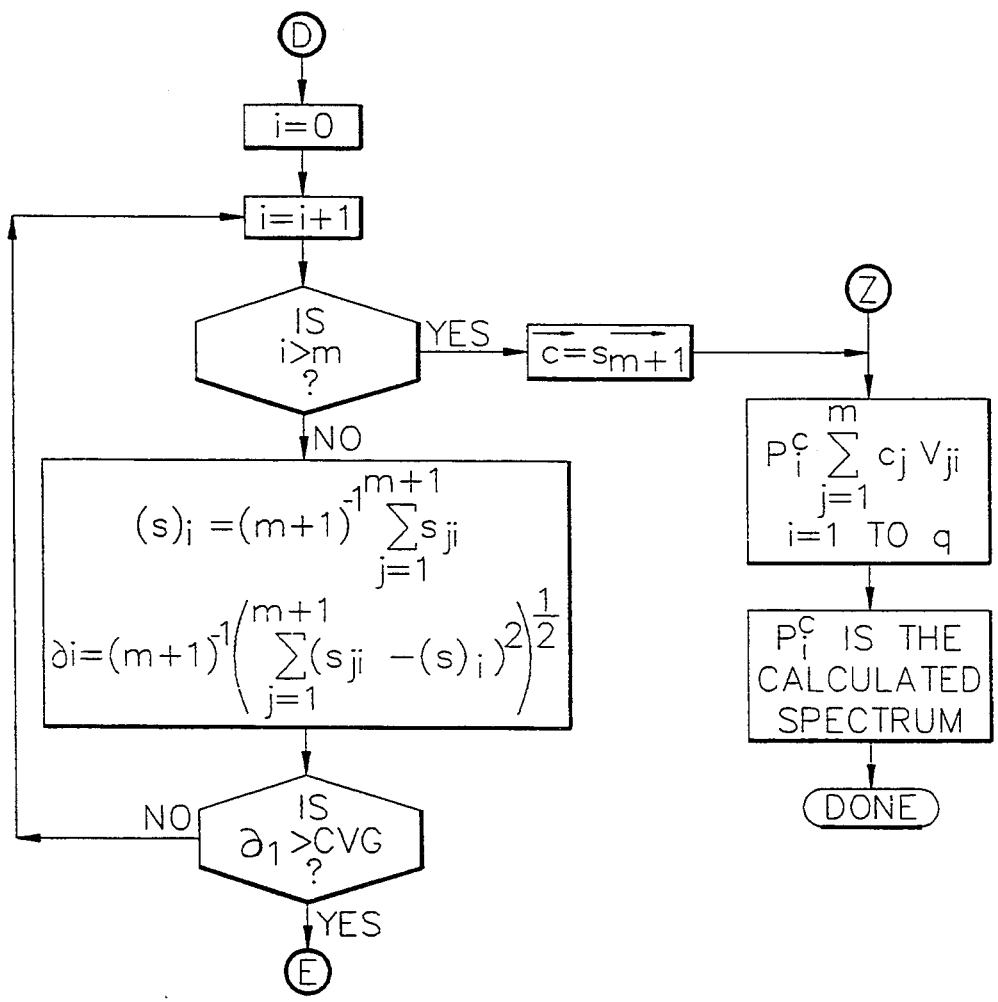
Figure 6F:
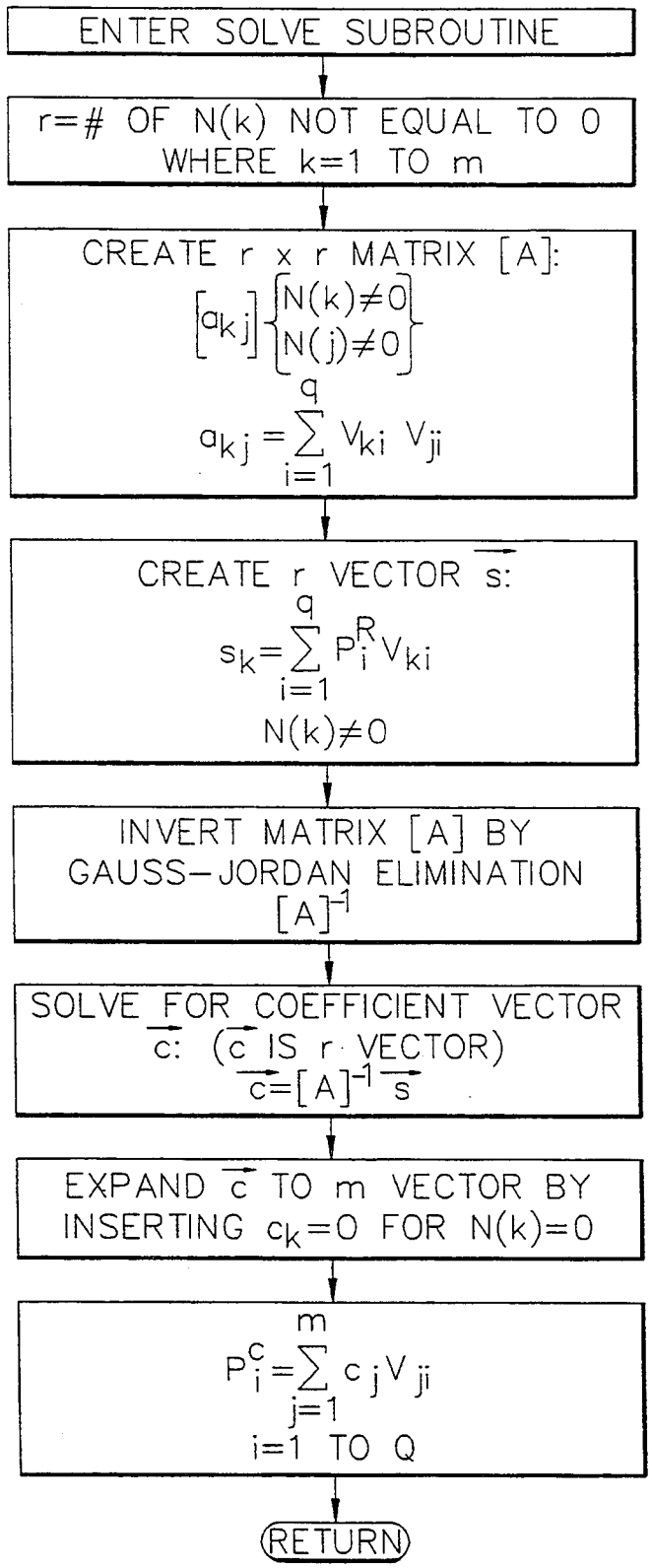
Figure 6G:
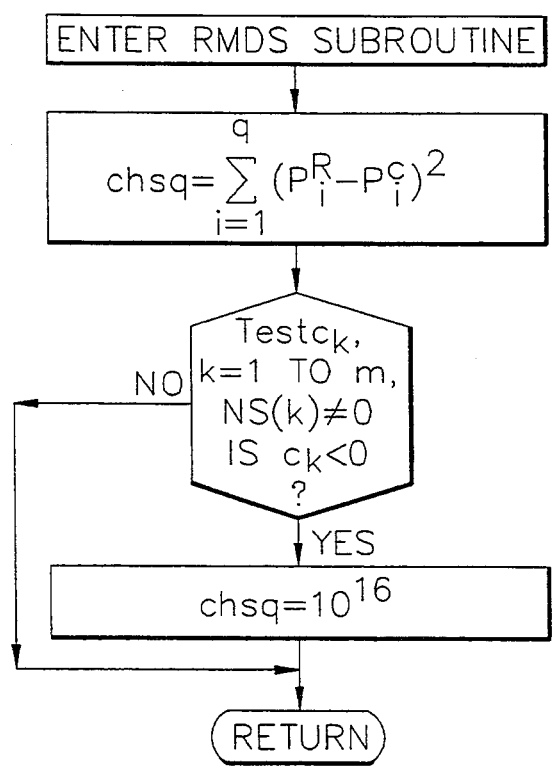

The absence of a VLDL component in the sample reflected in FIG. 3 is also reflected in FIG. 4, which is an Agarose Gel Filtration Profile showing the lipoprotein constituent concentrations for the samples reflected in FIGS. 2 and 3. The gel filtration process, the results of which are shown in FIG. 4, separates the lipoproteins of the plasma by particle size. Because the size of the lipoprotein particles is related to their density, FIG. 4 also indicates the relative densities of the lipoprotein constituents of the plasma. As shown in FIG. 4, the tracing 30 corresponds to the sample utilized in FIG. 2 and the tracing 31 corresponds to the sample utilized in FIG. 3. As can be seen in FIG. 4, the profile 30 has a large peak corresponding to the presence of VLDL in the sample. The profile 31 has little if any peak corresponding to the presence of VLDL. These differences are reflected in FIGS. 2 and 3 by the presence of the large V4 subclass in FIG. 2 and the relatively small V6 subclass in FIG. 3. FIG. 4 further illustrates the effect of different subclass distributions within a major lipoprotein class. As shown in FIG. 4, the LDL peak of tracing 30 occurs at higher elution volumes than does the LDL peak for tracing 31. The higher elution volumes of the LDL peak indicates a higher concentration of smaller LDL subclasses in the sample represented in FIG. 2, as indicated by the presence of L4 and L6, than was found in the sample represented in FIG. 3, which comprised L4 and L1 components.

FIG. 5 is a series of graphs illustrating the size distributions within the major lipoprotein classes for the samples reflected in FIGS. 2, 3 and 4. The distributions were obtained utilizing an average of duplicate analyses of blood samples from two individuals. As shown in FIG. 5, variations in the distribution of the constituent subclasses of the major lipoprotein classes results in the variations of the major constituent peaks as seen in FIG. 4.

FIG. 6 is a flow chart of the program which may be executed on a suitable computer for performing the method of the present invention. The program implements a nonnegative linear least squares regression with simplex optimization. The implementation of the program, as shown in FIG. 6, is similar to that described in U.S. Pat. No. 4,933,844, column 9, line 11 through column 11 line 15 is incorporated herein by reference as if set out fully. However, the program as described in FIG. 6, limits the coefficients to positive values while only calculating the real values of the coefficients, thereby reducing the matrices to ½ their original size. The program described in FIG. 6, further adds the simplex optimization to further refine the coefficient values. As shown in FIG. 6, the program is capable of accepting a plurality of reference spectra representing subclasses of lipoprotein classes and protein.

In the preferred embodiment, the NMR measurements are conducted at 250 MHz using an unmodified commercial spectrometer, model WM250 manufactured by Bruker Instruments, Inc. A fixed-frequency 5 mm $^1$H probe is installed and the temperature controller is set to 23° C. (+/−0.5° C.). Field homogeneity is optimized by shimming on a sample of 99.8% D2O until the spectral linewidth of the HDO NMR signal is less than 0.6 Hz. The 90° RF excitation pulse width is set to a value of 5.5+/−0.2 microseconds for the D2O measurement.

Figure 7:
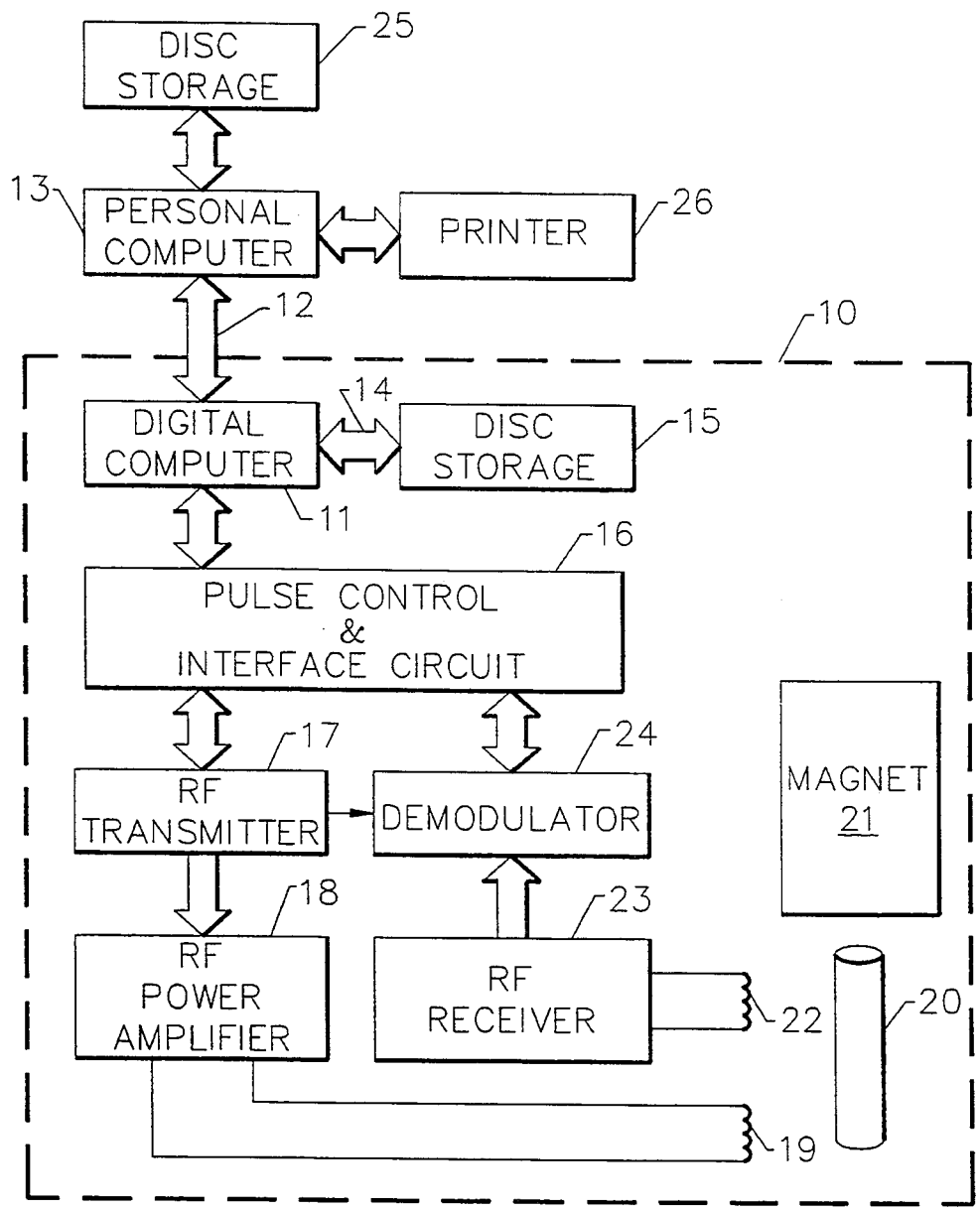
FIG. 7 is a block diagram of the apparatus employed to practice the present invention.

Referring particularly to FIG. 7, the spectrometer indicated by dashed line 10 is controlled by a digital computer 11. The computer 11 is sold under the trade name "ASPECT 2000" and it has a 24-bit word length and storage for 80K words. It is particularly well suited for performing fast Fourier transformations and includes for this purpose a hard-wired sine table and hard-wired multiply and divide circuit. It also includes a data link 12 to an external personal computer 13, and a direct-memory-access channel 14 which connects to a hard disc unit 15.

The digital computer 11 also includes a set of analog-to-digital converters, digital-to-analog converters and slow device I/O ports which connect through a pulse control and interface circuit 16 to the operating elements of the spectrometer. These elements include an RF transmitter 17 which produces an RF excitation pulse of the duration, frequency and magnitude directed by the digital computer 11, and an RF power amplifier 18 which amplifies the pulse and couples it to the RF transmit coil 19 that surrounds sample tube 20. The NMR signal produced by the excited sample in the presence of a 5.875 Tesla polarizing magnetic field produced by superconducting magnet 21 is received by a coil 22 and applied to an RF receiver 23. The amplified and filtered NMR signal is demodulated at 24 and the resulting quadrature signals are applied to the interface circuit 16 where they are digitized and input through the digital computer 11 to a file in the disc storage 15.

After the NMR data is acquired from the sample in the tube 20, it is processed by the computer 11 to produce another file which is stored in the disc storage 15. This second file is a digital representation of the chemical shift spectrum and it is subsequently read out to the personal computer 13 for storage in its disc storage 25. Under the direction of a program stored in its memory, the personal computer 13 processes the chemical shift spectrum in accordance with the teachings of the present invention to print a report which is output to a printer 26.

It should be apparent to those skilled in the art that the functions performed by the personal computer 13 and its separate disc storage 25 may also be incorporated into the functions performed by the spectrometer's digital computer 11. In such case, the printer 26 is connected directly to the digital computer 11. Prior to their measurement, the 0.5 ml reference samples are removed from the refrigerator and allowed to rise to a temperature of 23° C. for a period of from ten minutes to two hours. A sealed coaxial insert (Wilmad, Cat.#WGS-SBL) containing an external standard used for field-frequency lock and normalization of the plasma signal amplitudes is placed into each plasma NMR sample tube before the spectrum is run. The composition of this standard insert is 0.008M TSP (sodium 3-trimethyl [2,2,3,3-$^2$H4] propionate), 0.6 mMMnSO4, 99.8% D2O. The D2O provides the field-frequency lock signal and the integrated area of the TSP resonance is used to normalize the amplitudes of the plasma lipid resonances to correct for variations in spectrometer detection sensitivity. The solution is doped with $Mn^{2+}$ to paramagnetically broaden the normally sharp TSP resonance to make its integrated area insensitive to small differences in field homogeneity and to shorten its T1 relaxation time to a value comparable to those of the plasma lipid resonances (200 to 500 milliseconds). The reference sample containing the coaxial insert is placed at a defined depth in the sample tube and placed in the spectrometer. The sample is spun at a rate of 20 Hz. After locking on the $D_2O$ signal from the coaxial insert, a brief shimming of the z and $z^2$ gradient controls is performed using the NMR signal of the plasma water.

The reference spectra is then acquired using a standard one-pulse sequence preceded by a one second selective decoupler presaturation pulse of the strong $H_2O$ resonance. A spatially selective composite 90° observation pulse ($90_x - 90_y - 90_{-x} - 90_{-y}$) is used to minimize water suppression artifacts as described by A. Bax, "A Spatially Selective Composite 90o Radiofrequency Pulse", in J. Magn. Reson. 65, 142–145 (1985), although a normal 90° pulse also gives satisfactory results. The following acquisition parameters are used: 240 transients (4 dummy scans), 4K data size, quadrature detection, 2800 Hz spectral width (9.9 to −1.2 ppm), 0.73 sec. acquisition time, 1.0 sec. decoupler presaturation pulse (0.2 watt) at the $H_2O$ frequency, 22 microsecond composite 90o pulse, and constant receiver gain for all spectra. The time-domain spectra (FIDs) of the four lipoprotein reference samples are digitized and stored on computer disk.

The reference sample FIDs are processed identically to give the frequency-domain spectra used for the plasma lineshape fitting analysis. The processing operations of Fourier transformation, phasing, and baseline correction are accomplished using the standard commercial software of the NMR spectrometer (Bruker "DISNMR" program). The FIDs are Fourier transformed using 16K data points after application of a 1.0 Hz linebroadening exponential multiplication function. All spectra are scaled identically. The spectra are then phase corrected to give pure absorption mode signal.

The system is now ready to measure plasma samples. The procedure is virtually the same as that described above for measurement of the reference samples. The same NMR spectrometer is used and it is set up to operate in the identical fashion used to acquire the lipoprotein reference spectra. The time domain spectrum (FID) of the plasma sample is acquired in the identical fashion as the reference spectra and it is processed in the same manner to produce a digitized representation of the blood plasma sample spectrum in the disk of the personal computer- The whole plasma spectrum is then accurately referenced to the sharp NMR resonance peak produced by the calcium complex of EDTA which is present in the sample. The sample spectrum and the reference spectra are shifted as needed to align the CaEDTA peak at 2,519 ppm on the horizontal scale.

The mathematics used in the lineshape fitting process (i.e. non-negative linear least squares fit with simplex optimization of an unknown function in terms of a weighted sum of known functions) is well known and is described in many textbooks of numerical analysis and in articles such as D. J. Leggett, Numerical Analysis of Multicomponent Spectra, *Analytical Chemistry* 49, 276–281 (1977). A program for performing this function on a PC-AT computer is described by the flow chart in FIG. 6.

EXAMPLE 1

Blood is collected from healthy subjects after a 12 to 14 hour fast into Vacutainer Tubes (Becton Dickinson, Rutherford, N.J.) containing EDTA (final EDTA concentration, 1 g/L). Plasma is separated within 2 hours by centrifugation (2000×g, 20 minutes) and stored at 4° C. Plasma and lipoprotein lipids are analyzed by automated procedures at a hospital clinical laboratory. Total cholesterol and triglyceride concentrations are measured enzymatically with a Hitachi 717 analyzer (Boehringer Mannheim Diagnostics, Indianapolis, Ind.). HDL-C is measured with an Ektachem 700 analyzer (Eastman Kodak, Rochester, N.Y.) in the supernate obtained after precipitation of a plasma aliquot with dextran sulfate ($M_T$ 50,000)-$Mg^{2+}$.

Fasting plasma samples are fractionated into their lipoprotein subclass components according to density by sequential flotation ultracentrifugation at 4° C. as described by Schumaker and Puppione, *Methods in Enzymology* 128, 1–68 (1988). The following components are isolated: VLDL (d<1.006 kg/L), large LDL (d=1.006–1.035 kg/L), small LDL (d=1.035–1.063 kg/L), $HDL_2$ (d=1.063–1.125, $HDL_3$ (d=1.125–1.21 kg/L), and Protein (d>1.21 kg/L). Chylomicrons (d<0.940 kg/L) are isolated from plasma samples of subjects fed a fat-rich meal according to the procedure of Hatch and Lees, *Adv. Lipid Res.* 6, 1–68 (1968).

The above lipoprotein components from several subjects are combined to provide the standard samples used to generate the reference spectra employed in the computer lineshape analysis of the plasma spectra. To ensure a uniform ionic composition, which is essential for correct alignment of the reference spectra, each lipoprotein component solution is dialyzed for 24 hours at 4° C. against three changes of dialysate. The dialysate contains 120 mmol KCl, 5 mmol of EDTA, 1 mmol of $CaCl_2$, and 1 g of $NAN_3$, pH 7.4) Each component is then concentrated at 4° C. to about fivefold its normal plasma concentration using a Centricoh-10 microconcentrator (Amicon, Inc.) and then stored at 4° C. prior to NMR analysis.

All spectra of the isolated lipoprotein components and the real and artificial plasma samples are acquired under identical conditions at 250 MHz with a Bruker WM-250 spectrometer (Bruker Instruments, Billerica, Mass.). Samples (0.5 mL) in 5-mm (o.d.) NMR tubes are stored at 4° C. for as long as six days before being analyzed. A systematic study of the effect of sample storage conditions on plasma methyl and methylene lineshape indicates that spectral changes of samples kept at 4° C. are negligible for the first six days, but occasionally are apparent after longer storage (notably for plasma with high concentrations of triglyceride). Before placing samples in the spectrometer, they are allowed to equilibrate for 15–30 minutes at room temperature. A sealed coaxial insert, containing an external intensity standard (sodium 3-trimethylsilyl[2,2,3,3-$^2H_4$]propionate), was used as previously described in Otvos et al., *Clin. Chem.* 37, 369–376 (1991). Each NMR sample is placed at a reproducible, defined depth in the proton probe and allowed to equilibrate for 5 minutes at the chosen sample temperature (15-°45° C.). The probe is detuned by several megahertz to prevent radiation damping, which increases the 90° pulse length from 6 to 16 $\mu s$. Spectra are run locked with the sample spinning (20 Hz) and the magnetic field homogeneity is optimized for each sample by shimming on the water signal. A spatially selective composite 90° observation pulse is used to minimize water suppression artifacts, although a normal 90° pulse also gives satisfactory results. The spectral width is set to 2800 Hz, the data size is 4K, the acquisition time is 0.73 sec., the composite pulse length is 64 $\mu s$, and the number of transients is 120 with 4 dummy scans and constant receiver gain. The time-domain data are zerofilled to 16K multiplied by a 1-Hz exponential line-broadening function, and Fourier-transformed with identical scaling. After phasing and chemical shift referencing to the sharp CaEDTA resonance at 2.519 ppm, a linear baseline was applied as a correction to flatten the baseline between 1.8 and −0.2 ppm.

The Fourier-transformed plasma spectra and those of the pure lipoprotein reference samples are stored on the magnetic disk of an IBM-compatible PC--AT computer after transfer from the Aspect 2000A computer of the Bruker spectrometer by use of the FASTRAN program (University of Wisconsin-Madison). The linear least-squares analysis of the lineshape of the plasma methyl lipid resonance is performed by using a program written in BASIC- This program first places the real and imaginary data points from the methyl region of the plasma and lipoprotein reference spectra into separate arrays in computer memory, Several additional "approximated" reference spectra are also added into computer memory to account for known lipoprotein subclass size/density heterogeneity (and hence spectral heterogeneity) beyond that already accounted for by the subclasses isolated to provide the lipoprotein reference spectra (chylomicrons, VLDL, large and small LDL, HDL$_2$, HDL$_3$, and protein). The "approximated" reference spectra are created by digitally shifting the methyl regions of the lipoprotein component spectra to the left or right (downfield or upfield) by an appropriate amount. Thus, the chylomicron spectrum (V2) is shifted two data points (0.68 Hz) to the left and right to create artificial spectra V1 and V3, respectively, to represent a larger and smaller population of chylomicron particles. Similarly, the VLDL spectrum (V6) is shifted to the left by two data points (V4) and one data point (V5) and to the right by one data point (V7) to represent a wider range of VLDL particle sizes. The large LDL spectrum (L2) is shifted left (L1) and right (L3) by 1 data point as is small LDL (L5) to give spectra representative of "larger" (L4) and "smaller" (L6) small LDL. The HDL$_2$ spectrum (H2) was shifted left (H1) and right (H3) by two data points and the HDL$_3$ spectrum (H5) one data point to the left (H4) and right (H6) to give a total of six HDL subclass spectra representative of the range of HDL particle sizes expected. Thus, including the spectrum of the Protein component (d>1.21 kg/L), the plasma lineshapes are fit using a total of 20 reference spectra: V1–V7 representative of chylomicron and VLDL constituents, L1–L6 representative of LDL subclasses, and H1–H6 representative of the HDL subclasses (in the numbering system used, the larger numbers designate subclasses of smaller particle diameter or greater density).

The lineshape deconvolution is achieved with a nonnegative linear least-squares program described by Lawson et al., *Solving Least Squares Problems*, (Prentice Hall, 1974) that introduces the physical constraint that the derived concentrations must be positive. The latter constraint is necessary when fitting plasma samples that included in may not contain one or more of the components the fit, because experimental errors in the data (noise) often cause the calculation to give negative concentrations for these components. For example, including a chylomicron component in the analysis of fasting plasma samples will frequently give negative chylomicron concentrations (and hence incorrect concentrations for the other lipoprotein constituents) when the unconstrained least-squares method is used.

Mathematically, the methyl lineshape analysis is described by the following equation: .

$$P_i^R \approx \sum_{j=1}^{n} c_j^R V_{ji}^R + (c_k^R V_{ki}^R + c_k^I V_{ki}^I) + c_p^I V_{ji}^I$$

where the superscripts R and I denote the real and imaginary parts of the spectra; $P_i$ is the experimental plasma spectrum, consisting in this case of 132 discrete data points; $V_{ji}$ are the reference spectra of the n lipoprotein components; $V_{id}$ is the spectrum of the "protein" component; and $c_j$, $c_k$, and $c_p$ are the unknown relative concentrations whose values are determined by minimizing the root mean square deviation between the experimental plasma spectrum and the calculated spectrum.

The relative lipoprotein concentrations, $c_j$, derived by this method have no absolute meaning since they only relate the concentrations of the lipoprotein components of the plasma sample to those of the reference components of arbitrary concentration. However, if the concentrations of the lipoprotein solutions used to provide the standard reference spectra have been accurately determined by chemical analysis (i.e., by cholesterol analysis or, in the case of VLDL, by triglyceride analysis) the relative concentrations, $c_j$, derived from the lineshape analysis can be readily multiplied by these chemical concentrations to give lipoprotein concentrations expressed in the usual terms of lipoprotein cholesterol or triglyceride concentrations. If total chylomicron, VLDL, LDL, and HDL concentrations are desired, they are obtained simply by adding the derived concentrations of the individual subclasses (V1-V3, V4-V7, L1-L6, and H1-H6 respectively). Note that, if chylomicrons are treated as a subclass of VLDL, then VLDL concentration is obtained from V1-V7. If profiles of the lipoprotein subclass distributions are desired, they are provided directly by the relative concentrations of the subclass components used in the lineshape fitting algorithm. Alternatively, a single "size distribution parameter" that gives the weighted average particle size within a given class of lipoproteins may readily be calculated.

The methyl resonance lineshape of chylomicrons is very similar to that of VLDL, but the signal is shifted slightly downfield. To determine the effect of the presence of high concentrations of chylomicrons on the quantification of VLDL, LDL, and HDL by lineshape fitting, we analyzed by NMR and chemical methods both fasting and nonfasting plasma samples from individuals fed a fat-rich meal. The presence of chylomicrons in the postprandial sample is easily discerned by the altered position of the plasma peak maximum. By including chylomicrons as a fifth component in the lineshape analysis, where only four other components corresponding to the major lipoprotein classes were used, we obtained an excellent fit of the experimental plasma spectrum, but also found the derived concentrations of VLDL, LDL, and HDL to be nearly identical to those in the fasting state (see Table 3 below). These and similar results obtained for other postprandial samples indicate that lipoproteins can be reliably analyzed in nonfasting plasma by NMR. In contrast, the widely used method of Friedewald et al., *Clin. Chem.* 18, 499–502 (1972) has an absolute requirement for fasting samples because the accuracy of LDL-C values is severely compromised by the presence of chylomicrons.

TABLE 2

Influence of Chylomicrons on the NMR Lipoprotein Assay

| Sample | Plasma Lipid Concentration, g/L | | | |
|---|---|---|---|---|
| | TG | TC | HDL-C | LDL-C |
| Fasting | 2.21 | 1.88 | 0.41 | 1.03 |
| 2 h postprandial | 4.47 | 1.91 | 0.40 | 0.66 |
| 4 h postprandial | 6.20 | 1.87 | 0.37 | 0.26 |

| Sample | NMR-derived lipoprotein concn, mmol/L proton | | | |
|---|---|---|---|---|
| | Chylomicrons | VLDL | LDL | HDL |
| Fasting | — | 19.0 | 13.5 | 10.6 |
| 2 h postprandial | 22.4 | 19.2 | 13.3 | 9.9 |
| 4 h postprandial | 32.4 | 17.9 | 12.9 | 10.8 |

The information derived from the above procedure, which is very rapid (minutes) and requires almost no sample manipulation, is equivalent to that provided by acquiring separate spectra of the components prepared by ultracentrifugation (days) and comparing the integrals of their lipid NMR signals to those of reference lipoprotein samples. It is important to note that what is being measured by this procedure (NMR signal amplitude originating from the "mobile" lipid molecules in each class of lipoprotein) is related to, but fundamentally different from, lipoprotein lipid and protein concentrations derived by the various chemical and immunochemical assays in current clinical use. There is thus no reason to expect a perfect correlation to exist between these NMR-derived lipoprotein levels and those derived from standard serum cholesterol and triglyceride analyses. Despite well documented limitations in the accuracy and precision of the latter measurements, they are in widespread clinical use because of their proven value in assessing coronary heart disease risk and other lipid-related disease states. It is possible that lipoprotein levels derived from the NMR lineshape deconvolution process may have even greater diagnostic utility, but this will not be known until extensive clinical correlation studies have been performed.

It should be apparent to those skilled in the art that many variations are possible from the above-described preferred embodiment of the invention. For example, the polarizing field strength may be increased to further spread the NMR spectrum and to thereby improve the resolution of the deconvolution process. Also, the measurements may be conducted at other temperatures. Regardless of the magnetic field strength or the measurement temperature which is chosen, it is important that the chosen values remain constant throughout the process of producing the reference spectra and the sample spectra.

That which is claimed is:

1. A method of measuring the lipoprotein constituents of blood, comprising:
   storing the NMR spectra of a plurality of lipoprotein classes as reference spectra for said classes, said storing step further comprising storing the NMR spectra of a plurality of subclasses for at least one of said lipoprotein classes as reference spectra for the subclasses of said lipoprotein class;
   acquiring an NMR signal produced by a plasma or serum sample in an NMR spectrometer;
   producing an NMR spectrum of the sample by transforming the acquired signal;
   aligning a control peak in the sample spectrum to a corresponding control peak in the reference spectra wherein said control peak responds to the environmental variables in the same manner as the lipoproteins;
   producing a calculated lineshape by adding together the stored reference spectra in amounts determined by respective non-negative reference spectrum coefficients; and
   adjusting the reference coefficients to fit the calculated lineshape to the NMR spectrum of the sample.

2. A method of measuring the lipoprotein constituents of blood according to claim 1 further comprising the step of calculating the concentration of at least one major lipoprotein class or subclass thereof as a function of the value of the reference coefficients.

3. A method of measuring the lipoprotein constituents of blood according to claim 1 in which the lipoprotein subclasses are selected from the group consisting of the subclasses of VLDL, LDL, HDL and chylomicrons.

4. A method of measuring the lipoprotein constituents of blood according to claim 1 in which the NMR spectrum includes the peak produced by methyl protons.

5. A method of measuring the lipoprotein constituents of blood according to claim 1 in which the calculated lineshape is fit to the NMR spectrum of the sample by minimizing the root mean square error.

6. A method of measuring the lipoprotein constituents of blood according to claim 1 in which the calculated lineshape is fit to the NMR spectrum of the sample through nonnegative linear least squares deconvolution.

7. A method of measuring the lipoprotein components of blood according to claim 1 wherein said sample control peak is an EDTA peak.

8. A method of measuring the lipoprotein constituents of blood, comprising:
   storing the NMR spectra of a plurality of lipoprotein classes as reference spectra for said classes, said storing step further comprising storing the NMR spectra of chylomicrons as reference spectra for chylomicrons;
   acquiring an NMR signal produced by a plasma or serum sample in an NMR spectrometer;
   producing an NMR spectrum of the sample by transforming the acquired signal;
   aligning a control peak in the sample spectrum to a corresponding control peak in the reference spectra wherein said control peak responds to the environmental variables in the same manner as the lipoproteins;
   producing a calculated lineshape by adding together the stored reference spectra in amounts determined by respective non-negative reference spectrum coefficients; and
   adjusting the reference coefficients to fit the calculated lineshape to the NMR spectrum of the sample.

9. A method of measuring the lipoprotein constituents of blood according to claim 8 further comprising the step of calculating the concentration of at least one major lipoprotein constituent as a function of the value of the reference coefficients.

10. A method of measuring the lipoprotein constituents of blood according to claim 8 in which the NMR spectrum includes the peak produced by methyl protons.

11. A method of measuring the lipoprotein components of blood according to claim 8 in which the calculated lineshape is fit to the NMR spectra of the sample through nonnegative linear least squares deconvolution.

12. A method of measuring the lipoprotein components of blood according to claim 8 wherein said sample control peak is an EDTA peak.

13. An apparatus for measuring the lipoprotein constituents of blood, comprising:

means for storing the NMR spectra of a plurality of lipoprotein classes as reference spectra for said classes, said storing step further comprising storing the NMR spectra of a plurality of subclasses for at least one of said lipoprotein classes as reference spectra for the subclasses of said lipoprotein class;

means for acquiring an NMR signal produced by a plasma or serum sample in an NMR spectrometer;

means for producing an NMR spectrum of the sample by transforming the acquired signal;

means for aligning a control peak in the sample spectrum to a corresponding control peak in the reference spectra wherein said control peak responds to the environmental variables in the same manner as the lipoproteins;

means for producing a calculated lineshape by adding together the stored reference spectra in amounts determined by respective non-negative reference spectrum coefficients; and means for adjusting the reference coefficients to fit the calculated lineshape to the NMR spectrum of the sample.

14. An apparatus for measuring the lipoprotein constituents of blood according to claim 13 further comprising means for calculating the concentration of at least one major lipoprotein class or subclass thereof as a function of the value of the reference coefficients.

* * * * *

UNITED STATES PATENT AND TRADEMARK OFFICE
CERTIFICATE OF CORRECTION

PATENT NO. : 5,343,389
DATED : 30 August 1994
INVENTOR(S) : James D. Otvos

It is certified that error appears in the above-indentified patent and that said Letters Patent is hereby corrected as shown below:

Column 8, line 53, please correct "SBL" to read --8BL--.

Column 9, line 51, please correct "2,519" to read
    -- 2.519 --.

Column 11, line 60, please delete "included in".

Column 11, line 61, please insert after components
    -- included in --.

Column 14, Claim 1, line 5, please correct "spectrum" to
    read -- spectra --.

Signed and Sealed this

Thirteenth Day of December, 1994

Attest:

BRUCE LEHMAN

*Attesting Officer*    *Commissioner of Patents and Trademarks*